United States Patent [19]

Loos et al.

[11] Patent Number: 4,663,032
[45] Date of Patent: May 5, 1987

[54] APPARATUS FOR DECANTING OF A BLOOD-PLASMA LAYER AND A BUFFY-COAT LAYER FROM A CENTRIFUGE-BLOOD BAG

[75] Inventors: Johannes A. Loos; Willem Eitjes; Johannes C. G. H. de Bruyn, all of Amsterdam, Netherlands

[73] Assignee: NPBI Nederlands Produktielaboratorium voor Bloedtransfusieapparatuur en Infusievloeistoffen B.V., Emmer-Compascuum, Netherlands

[21] Appl. No.: 734,359

[22] Filed: May 14, 1985

[30] Foreign Application Priority Data

May 14, 1984 [DE] Fed. Rep. of Germany ....... 3417892

[51] Int. Cl.$^4$ ...................... B01D 21/26; B01D 21/32
[52] U.S. Cl. .................... 210/97; 210/513; 210/927; 222/103; 222/214
[58] Field of Search ................ 210/97, 109, 134, 513, 210/515, 516, 523, 927; 222/95, 96, 103, 214; 251/7

[56] References Cited

U.S. PATENT DOCUMENTS 3,513,976 5/1970 James .............................. 210/361 X
4,040,959* 8/1977 Berman et al. ................. 210/516 X
4,284,209 8/1981 Barbour, Jr. .................... 222/103 X
4,350,585 9/1982 Johansson et al. ............... 210/97 X
4,430,078 2/1984 Sprague .......................... 222/95 X
4,482,342 11/1984 Lueptow et al. ............... 210/927 X

FOREIGN PATENT DOCUMENTS 58-11854 1/1983 Japan ................................. 210/927

OTHER PUBLICATIONS

Vox Sanguinis, 39 (1980) 48–51.

Primary Examiner—Richard V. Fisher
Assistant Examiner—W. Gary Jones
Attorney, Agent, or Firm—Karl F. Ross; Herbert Dubno

[57] ABSTRACT

A press for driving a plasma layer and a buffy-coat layer in succession out of a centrifuged whole blood bag which has upper and lower press plates between which a clamping element is displaceable, all juxtaposed with a stationary plate so that after displacement to the lower press plate to drive off plasma and operation of the upper press plate to spread the buffy-coat layer in height, the clamping element can be actuated to clamp off the bag between the buffy-coat layer and the red cell concentrate so that advance of the upper press plate can drive off the buffy-coat layer.

17 Claims, 2 Drawing Figures

४,६६३,०३२

APPARATUS FOR DECANTING OF A BLOOD-PLASMA LAYER AND A BUFFY-COAT LAYER FROM A CENTRIFUGE-BLOOD BAG

FIELD OF THE INVENTION

Our present invention relates to an apparatus for the decanting, successively, of an upper blood-plasma layer and an intermediate buffy-coat layer through a flexible tube opening into the top of a flexible bag containing blood which has been centrifuged to form these two layers above the erythrocyte or red blood cell concentrate.

BACKGROUND OF THE INVENTION

It is known that the centrifugation of blood can separate the latter into three distinct layers, namely a least-dense layer constituted by the blood plasma and forming the upper layer, an intermediate layer consisting predominantly of leukocytes and thrombocytes, known as the buffy-coat layer and of intermediate density, and a lower layer constituted predominantly of erythrocytes or in the form of a red blood cell concentrate having the greatest density.

Separation of these layers is frequently desired so that, for example, the plasma can be stored separately from the red cell concentrate, the red cell concentrate can be processed into valuable blood products, and/or the buffy-coat layer can be processed for a similar purpose While the centrifugation of blood has been done in rigid vessels or in centrifuges which separate the components in a continuous manner, in recent years the collection of blood in flexible bags has dominated and so too has the whole blood been increasingly centrifuged in such bags which have flexible tubes opening into the upper ends of the bags.

In order to decant the plasma and buffy-coat layers from such bags, press arrangements have been provided which can have vertical press plates between which the bag can be introduced and one of each is advanced toward the other to drive the upper layer of plasma out of the tube followed by the buffy-coat layer.

Such a press generally made use of a movable press plate which was somewhat smaller in size than the stationary press plate and which covered substantially the area of the red cell concentrate so that by squeezing the latter inwardly, the layers above the red cell concentrate can be effectively driven out of the tube.

A press of this type is described in U.S. Pat. No. 4,350,585 and has experienced a problem at least with respect to the expulsion of the buffy-coat layer from the blood collection bag. In this arrangement, after the plasma is ejected by squeezing the red cell concentrate with the relatively small movable press plate, all or part of the buffy-coat layer tends to remain in the bag above this movable press plate and must be expelled from the bag manually or by other manipulations applied to the portion of the bag above the red cell concentrate. In practically all cases some mixing of the low-density buffy-coat layer with the red cell concentrate occurs and this is undesirable.

The successive removal of blood plasma and buffy coat from a blood bag has also been described in *Vox Sanguinis* 39 (1980), 46–59, see especially pages 48–51.

In this system after the blood plasma has been driven off above the buffy coat, a clamp is applied to the bag between the buffy coat and the red blood cell concentrate to allow the separation. A stomach-operation clamp is used for this purpose.

The quality of the separation here as well is dependent upon the manipulative skills of the individual.

OBJECTS OF THE INVENTION

It is the principal object of our present invention to provide an improved apparatus for the decanting of a plasma layer and a buffy-coat layer from a centrifuged whole blood bag whereby the disadvantages of the earlier apparatus can be avoided.

Another object of this invention is to provide an improved apparatus for the purposes described which is capable of automatically decanting in succession the plasma and the buffy-coat layer from centrifuged whole blood in a flexible bag without manual manipulations which may lead to mixing of the red cell concentrate and the buffy-coat layer and in a substantially automatic and highly precise manner.

SUMMARY OF THE INVENTION

These objects and others which will become apparent hereinafter are attained, in accordance with the invention, in a press apparatus of the type described wherein, however, an upper press plate is provided above the relatively small press plate previously described and likewise is juxtaposed with the fixed press plate and which is movable independently of the lower movable press plate so that it covers substantially the balance of the bag and at least an upper portion thereof, while between the upper and lower press plates, a horizontally movable squeezing element is provided for clamping the bag between itself and the stationary press plate.

Not only does this system integrate a clamp directly into the press, but it provides a unique arrangement for ensuring that the buffy-coat layer is fully decanted from the bag.

According to a feature of the invention, the upper and lower press plates and the squeezing or clamping element are disposed on the same side of the bag, preferably on the housing side thereof, so they can be actuated by respective drives while the stationary plate can be swingably mounted along one edge about a vertical axis and provided with means on the housing which can lock the stationary plate in position relative to the housing and to the movable plates. This locking arrangement facilitates insertion and removal of the bags.

Advantageously the upper press plate is provided with an elastic cushion with the aid of which a compressing force is applied to the upper movable press plate in the direction of the fixed press plate.

Control means can be provided to enable the upper press plate to be advanced before activation of the lower press plate with an adjustable partial stroke.

The bag can be suspended from pins which may be vertically adjusted, i.e. adjusted as to height relative to the housing.

According to a feature of the invention the bag squeezing or clamping element is juxtaposed with an elastic or resilient portion of the opposing fixed press plate while the lower press plate can have its actuating force relieved upon advance of the clamping element.

It has also been found to be important to control the advance of the clamping element with the aid of a sensing source for the blood plasma/buffy-coat interface, this sensing means being preferably a horizontal row of infrared light emitters or source and a row of infrared detectors spaced from the emitters across the transparent bag and being located advantageously substantially at the level of the upper movable press plate.

The infrared emitters and detectors are preferably designed to operate with a pulsing infrared with a wavelength of 940 nm and the pulsing frequency should be about 68 Hz.

A wavelength of 940 nm and a frequency of 68 Hz has been found to be especially effective for the detection of the interface between the buffy-coat layer and the plasma so that ambient effects are eliminated, namely, the effects of daylight, room lighting, bag distortion and the like.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
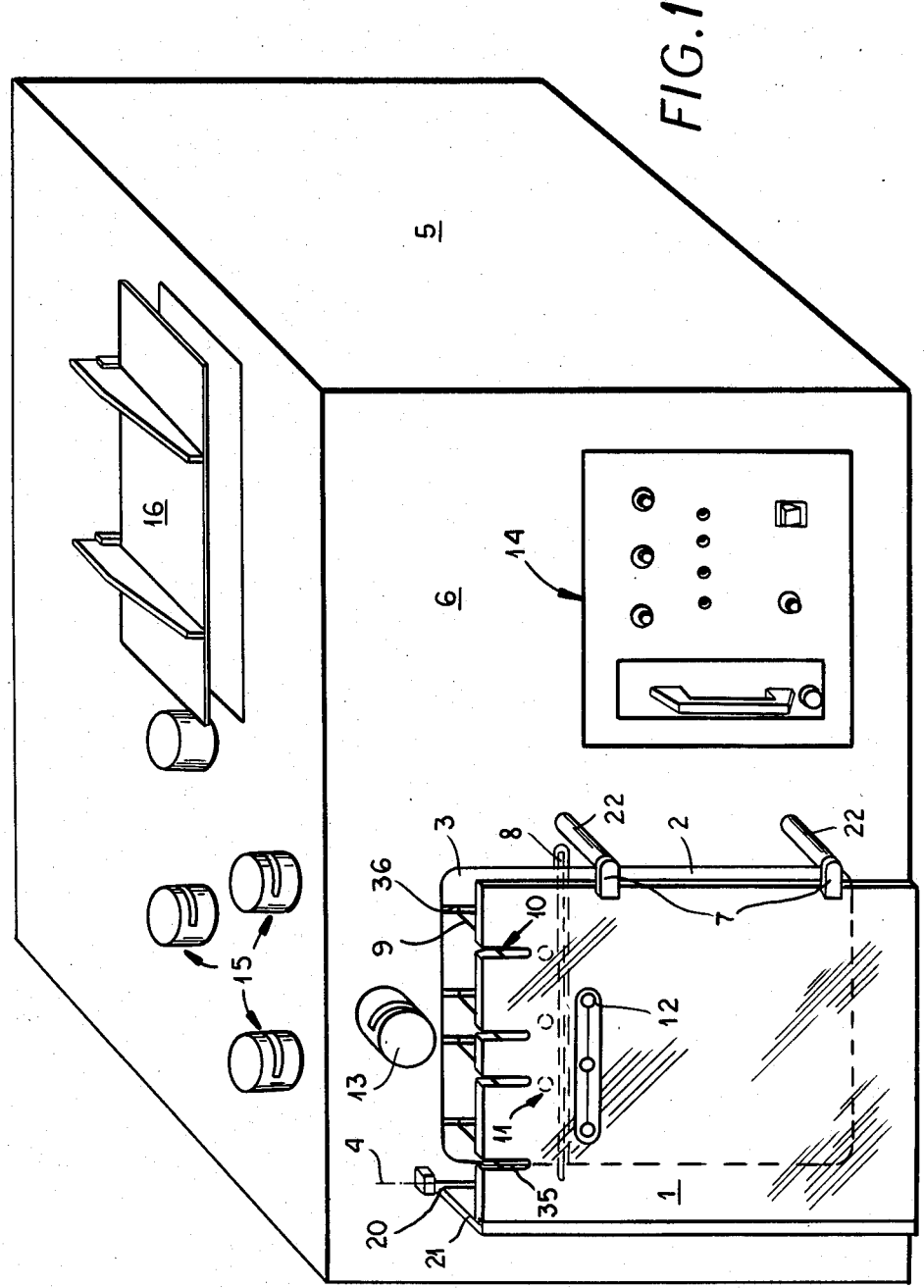
FIG. 1. is a perspective view in highly diagrammatic form of an apparatus in accordance with the present invention.
Figure 2:
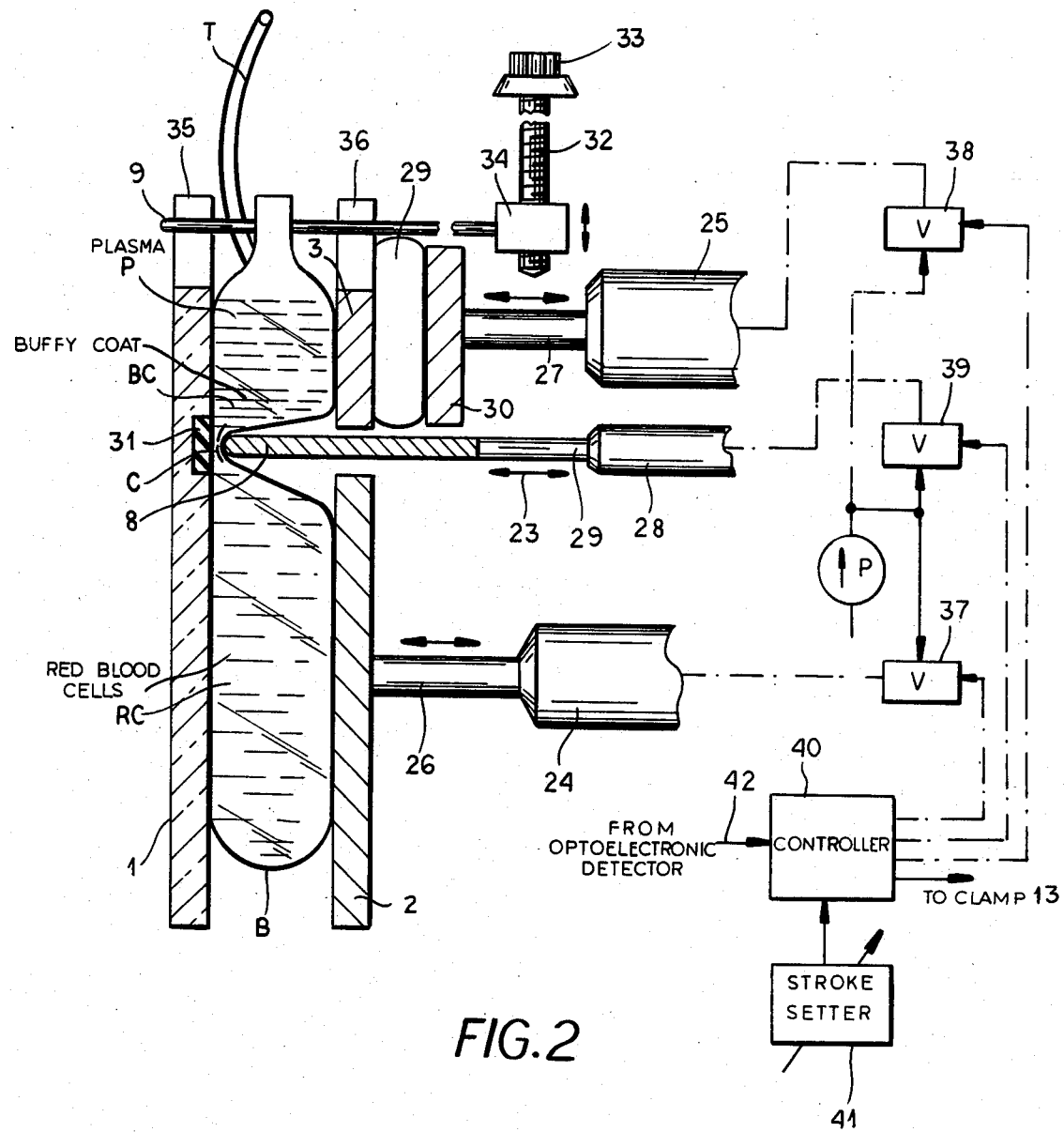
FIG. 2 is a diagrammatic vertical section through this apparatus in which the housing wall and structure have not been shown and in which the drives for the movable parts and the controls therefor have been illustrated only schematically.

The apparatus of the invention as illustrated in FIGS. 1 and 2 is intended to decant a plasma layer P overlying a buffy-coat layer BC above a red cell concentrate layer RC in a bag B containing whole blood which has been centrifuged to form the respective layers.

The flexible bag B is composed of transparent synthetic resin material, i.e. is a blood-collecting bag, and is provided with an upper tube T through which the layers can be driven out. A anticoagulant may have been provided in the blood collecting bag before the commencement of blood collection.

The apparatus for decanting the two upper layers from this bag comprises a housing 5 upon which a press plate 1 is mounted by a hinge 20 at a flange 21 rigid with this plate and along one vertical edge thereof so that the plate 1 can swing about the vertical axis 4.

A pair of swingable latches 7 on pedestals 22 can engage an opposite longitudinal edge of the plate 1 when the latter is parallel to the front wall 6 of the housing as shown in FIG. 1 to brace this plate and hold it stationary during press operation.

Before the plate 1 is swung into the position shown in FIG. 1, the bag B seen in FIG. 2 but omitted in FIG. 1, is inserted against the upper and lower press plates 3 and 2, respectively, which lie on the housing side of the device.

The lower press plate 2 has an area such that it encompasses at least the area containing the red cell concentrate RC of the bag. The upper press plate 3 covers the remainder of the area of the bag except for a portion between the two plates within which a clamping element 8 is provided.

The clamping element 8 between the upper and lower press plates 3 and 2 is itself a horizontally movable horizontal plate and can be displaced in the direction 23 (FIG. 2) to clamp the bag and define two compartments one above and one below the clamping site C.

Within the housing 5, the plates 2 and 3 are provided with independent drives 24 and 25, respectively, constituted by fluid-operated cylinders whose piston rods 26 and 27 are shiftable in opposite directions and can displace the plates 2 and 3 independently to the left and to the right. Preferably these drivers 24 and 25 are double-acting hydraulic cylinders.

A further double-acting hydraulic cylinder 28 has its piston rod 29 connected with the plate 8.

Although not visible in FIG. 2, it will be apparent that the press plate 3 can be actuated via an elastic cushion 29 bonded to the plate 3 and to a plate 30 to which the piston rod 27 is actuated. This elastic cushion compensates for irregularities in the bag and ensures a complete expulsion of the liquid contained in the upper compartment between the clamping site C and the tube T.

As is also apparent from FIG. 2, the stationary plate 1 in its region opposite the edge of the clamping plate 8 is provided with an elastic cushion 31 which serves to prevent damage to the bag by the clamping action.

At the level of the upper press plate 3, suspending pins 9 for the centrifuged bag are provided As can be seen from FIG. 1 these pins 9 can be provided in pairs so that bags of different sizes can be accommodated or bags of different constructions can be used in the system of the invention. The pins 9 are provided with means enabling their heights to be adjusted Such means can include, as is apparent from FIG. 2, a threaded spindle 32 which is journaled on the housing, has a adjustment knob 33 and threadedly engages a bar 34 to which the pins 9 are anchored.

To accommodate the vertical adjustability of the pins 9, the stationary press plate 1 and the movable press plate 3 are provided with vertical slits 35 and 36, respectively. Slits 35 and 36 are part of the combined set of slits 10.

The clamping element 8 is controlled by a sensing device for the blood plasma/buffy-coat interface, this sensing device being provided heightwise in the region of the upper press plate 3 in the form of a horizontally oriented row of infrared light emitters 11 and detectors 12 which are energized with pulsating light at a frequency of 68 Hz, the light having a wavelength of 940 nm.

These parameters have been found to eliminate detrimental effects of daylight and room light upon the interface detection and further enable the detector to be insensitive to writing on the bag and distortion thereof.

An operating signal is triggered only when all three pairs of light sources and light detectors 11, 12 have the transmitted light reduced by at least 80 % for at least 0.1 seconds To spread the buffy coat in height, before the lower press plate 2 is actuated, the upper press plate 3 is advanced through a portion of its stroke To this end, each of the drivers 24, 25, 28 is provided with a control valve shown only schematically at 37, 38 and 39, the valves being operated by a controller 40 which receives an input from the stroke setter 41 to advance the movable plate 3 by this portion of its total stroke initially By corresponding setting of this partial stroke and the height of the pins 9, practically all usual blood bags can be employed in accordance with the invention since the clamping element 8 can then be moved across the bag directly below the buffy-coat cell concentrating interface to subdivide the bag at this interface. When the clamping 8 is actuated, the lower press plate can be relieved to enable the clamping element to achieve the clamping operation as rapidly as possible.

Above the press, a tube clamp 13 is provided to hold the tube in place (see U.S. Pat. No. 4,350,585) and the housing can include the power supply and operating controls 14, including the 940 nm pulsed power supply for the infrared emitters The infrared sensor input to the controller 40 has been represented at 42. An auxiliary press for an auxiliary bag has been shown at 16 in FIG. 1 (see the discussion of satellite bags in the Vox Sanguinis article cited) and additional clamping tube-welding or sealing heads 15 can be provided as diagrammatically represented at 15. With the plate 1 swung open, the centrifuged blood bag is suspended on the pins 9 and its tube T is lead through the tube clamp 13.

The free end of the tube can be connected via other tubes in the clamping and welding heads 15 to two satellite for empty bags. The plate 1 is then closed and latched at 7. The clamp 15 for the plasma is opened while the clamp for the satellite bag for the buffy-coat layer is closed The upper press plate 3 is advanced through the aforementioned portion of its stroke to drive at least a part of the blood plasma into its satellite bag. The buffy-coat layer is thereby spread.

The lower press plate 2 is then advanced by the controller 40 to drive off additional blood plasma and raise buffy-coat/plasma interface. When this interface reaches the sensor pairs 11, 12, the clamp 13 is closed. The clamping element 8 is automatically advanced in the direction of arrow 23 and the force upon the lower press plate 2 is relieved. The buffy-coat layer is thereby separated from the red cell concentrate.

If all of the plasma has been driven off or when all of the plasma has been off, the clamp 15 seals off the connection with the plasma bag and another clamp 15 for the buffy-coat satellite bag is opened.

The plate 3 continues its advance through the remainder of its stroke to completely drive off the buffy-coat layer into its satellite bag.

Using the auxiliary press 16, an auxlary fluid (SAGM) can be added to the red cell concentrate layer through a respective branch tube in one of the clamps 15. The press 16 can be operated with drivers similar to those shown by the controller 40.

The lower press place 2 and the upper press plate 3 need not necessarily be rigid or exclusively horizontally displaceable and indeed it is possible to actuate these press plates by or form them as hydraulic or pneumatically actuatable membranes within this invention.

We claim:

1. An apparatus for decanting a blood plasma layer and a buffy-coat layer in succession from a centrifuged blood bag having said buffy-coat layer above a red cell concentrate and said plasma layer above said buffy-coat layer in said bag, said bag having a tube at an upper end thereof, said apparatus comprising:

a housing;

a vertical stationary press plate mounted on said housing and positionable against one side of said bag;

a lower movable press plate mounted between said housing and a lower portion of said stationary press plate positionable along an opposite side of said bag substantially encompassing a portion thereof containing said red cell concentrate;

an upper movable press plate displaceable independently of said lower press plate and mounted between said housing and an upper portion of said stationary press plate positionable along said opposite side of said bag above said lower press plate; and a clamping element mounted on said housing and displaceable thereon independently of said upper and lower press plate between said upper and lower press plates for squeezing said bag against said stationary press plate to define two compartments in said bag, one above and one below the clamping element.

2. The apparatus defined in claim 1, further comprising means for mounting said stationary press plate on said housing to enable it to swing about a vertical axis and enable said bag to be accommodated between said stationary press plate and said movable press plates, and latch means for securing said stationary press plate in a position in which it is substantially parallel to said movable press plates.

3. The apparatus defined in claim 2 wherein said upper press plate is provided with an elastic cushion allowing it to compensate for distortion of said bag.

4. The apparatus defined in claim 1, further comprising means for imparting an initial partial stroke to said upper press plate and thereby spread said buffy-coat layer in said bag in a vertical direction.

5. The apparatus defined in claim 1, further comprising a plurality of pins extending from said housing for suspending said bag therefrom, and means for vertically adjusting the level of said pins.

6. The apparatus defined in claim 1, further comprising an elastic member on said stationary plate juxtaposed with said clamping element.

7. The apparatus defined in claim 1, further comprising means for relieving a force on said lower press plate upon advance of said clamping element.

8. The apparatus defined in claim 1, further comprising means for sensing a blood plasma/buffy-coat interface for controlling said clamping element 9. The apparatus defined in claim 8 wherein said sensing means includes a row of infrared light detectors paired with respective infrared emitters across said bag.

10. The apparatus defined in claim 9 wherein said sensing means is operated with pulsating light at a wavelength of 940 nm.

11. The apparatus defined in claim 10, further comprising means for pulsing said light at a frequency of 68 Hz.

12. The apparatus defined in claim 11, further comprising means for mounting said stationary press plate on said housing to enable it to swing about a vertical axis and enable said bag to be accommodated between said stationary press plate and said movable press plates, and latch means for securing said stationary press plate in a position in which it is substantially parallel to said movable press plates 13. The apparatus defined in claim 12 wherein said upper press plate is provided with an elastic cushion allowing it to compensate for distortion of said bag.

14. The apparatus defined in claim 13, further comprising means for imparting an initial partial stroke to said upper press plate and thereby spread said buffy-coat layer in said bag in a vertical direction 15. The apparatus defined in claim 14, further comprising a plurality of pins extending from said housing for suspending said bag therefrom and means for vertically adjusting the level of said pins.

16. The apparatus defined in claim 15, further comprising an elastic member on said stationary plate juxtaposed with said clamping element 17. The apparatus defined in claim 16, further comprising means for relieving a force on said lower press plate upon advance of said clamping element.

* * * * *